United States Patent
Basile et al.

(10) Patent No.: US 11,587,463 B2
(45) Date of Patent: Feb. 21, 2023

(54) PATIENT TRAINING DEVICE FOR USE WITH A SAFETY SYRINGE INJECTOR

(71) Applicants: Peter A. Basile, Bloomsbury, NJ (US); Michael M. Maia, Colonia, NJ (US); Merck Sharp & Dohme Corp., Rahway, NJ (US)

(72) Inventors: Peter A. Basile, Bloomsbury, NJ (US); Michael M. Maia, Colonia, NJ (US)

(73) Assignee: MERCK SHARP & DOHME LLC, Rahway, NJ (US)

(*) Notice: Subject to any disclaimer, the term of this patent is extended or adjusted under 35 U.S.C. 154(b) by 979 days.

(21) Appl. No.: 16/338,797

(22) PCT Filed: Oct. 13, 2017

(86) PCT No.: PCT/US2017/056442
§ 371 (c)(1),
(2) Date: Apr. 2, 2019

(87) PCT Pub. No.: WO2018/075335
PCT Pub. Date: Apr. 26, 2018

(65) Prior Publication Data
US 2020/0043372 A1   Feb. 6, 2020

Related U.S. Application Data

(60) Provisional application No. 62/409,589, filed on Oct. 18, 2016.

(51) Int. Cl.
*G09B 23/28* (2006.01)
*A61M 5/315* (2006.01)
*A61M 5/32* (2006.01)

(52) U.S. Cl.
CPC ....... *G09B 23/285* (2013.01); *A61M 5/31515* (2013.01); *A61M 5/3275* (2013.01); *A61M 2205/583* (2013.01)

(58) Field of Classification Search
CPC ............ G09B 23/285; A61M 5/31501; A61M 5/31508; A61M 5/31515; A61M 5/3275;
(Continued)

(56) References Cited

U.S. PATENT DOCUMENTS 2,695,023 A    11/1954   Brown
6,872,190 B1    3/2005   Denis et al.
(Continued)

FOREIGN PATENT DOCUMENTS

WO    WO2016128977 A1    8/2016

*Primary Examiner* — Kami A Bosworth
*Assistant Examiner* — Antarius S Daniel
(74) *Attorney, Agent, or Firm* — Janet E. Fair; Alysia Finnegan (57) ABSTRACT

A reusable safety syringe training device is provided. The device comprises a syringe contained within a syringe protective member. The syringe protective member is movable vertically within an outer protective sheath from a first position to a second position and back to the first position. In the first position, the device is in an injection-ready position with the needle exposed and the syringe protective member in a locked vertical position with respect to the outer protective sheath. In the second position, the device is in a post-injection position such that the syringe protective member is no longer vertically locked with respect to the outer protective sheath and has moved vertically upward thereby rendering the needle within the outer protective sheath. The plunger carries a release flange sufficient to engage release latches that otherwise retain the syringe protective member in the first position. The release flange engages that release latches when the user pushes the plunger down to effectuate the injection. Once pressure is removed from the plunger after the injection has concluded, a springe mechanism drives the syringe protective member upwards to the second position. The user can then turn the plunger such that the release flange is no longer able to (Continued)

engage the release latches and push the plunger back down to lock the syringe protective member in its first position. The user is then able to pull the plunger back up while the syringe protective member remains locked, turn the plunger back to a position where the release flange is in a position to engage the release latches again, and perform another injection.

14 Claims, 7 Drawing Sheets

(58) Field of Classification Search
CPC .............. A61M 5/3205; A61M 5/3243; A61M 5/3245; A61M 5/326; A61M 5/20; A61M 2205/583; A61M 2205/584; A61M 2205/582; A61M 2205/6081; A61M 2005/3247; A61M 2005/3254; A61M 2005/3261; A61M 2005/3264
See application file for complete search history.

(56) References Cited

U.S. PATENT DOCUMENTS

| | | | |
|---|---|---|---|
| 7,468,054 B2 * | 12/2008 | Crawford | A61M 5/326 604/110 |
| 2013/0079717 A1 * | 3/2013 | Torris | A61M 5/3232 604/110 |
| 2013/0190783 A1 * | 7/2013 | Noda | A61F 2/0063 606/151 |
| 2018/0001032 A1 * | 1/2018 | Kleyman | A61M 5/31501 |
| 2018/0233066 A1 * | 8/2018 | Lettman | A61M 5/3221 |

* cited by examiner

PATIENT TRAINING DEVICE FOR USE WITH A SAFETY SYRINGE INJECTOR

CROSS-REFERENCE TO RELATED APPLICATIONS

This application is a U.S. National Phase application under 35 U.S.C. § 371 of PCT Application No. PCT/US2017/056422, filed Oct. 13, 2017, which published as WO2018/075335 A1 on Apr. 26, 2018, and claims priority under 35 U.S.C. § 365(b) from U.S. provisional patent application No. 62/409,589, filed Oct. 18, 2016.

BACKGROUND OF THE INVENTION

A wide variety of drugs are administered in prefilled syringes. To limit the potential for disease transmission, the majority of prefilled syringes are packaged within safety devices. These devices deploy at the end of injection and physically cover the needle, consequently preventing needle sticks and disease transmission due to these sticks. However, once the safety device is deployed, it is locked in place to prevent reuse.

To deliver needle stick protection, the patient or caregiver must use the safety device correctly; some level of training is required to obtain proficiency of use. Typically the drug contained within the syringe is expensive and therefore too costly to be used in a training environment. Placebo syringes are far cheaper, but still expensive; and they cannot be reused.

There is a need for a low cost, reusable safety syringe trainer that can be used as a teaching tool for the care giver and a practice tool for the patient.

SUMMARY OF THE INVENTION

The present invention provides reusable safety syringe devices for use as a teaching and practice tool. The safety syringe device of the present invention comprises four primary parts: (1) a first tubular member; (2) a second tubular member disposed within an inner annular cavity of the first tubular member; (3) a syringe secured within an inner annular cavity of the second tubular member; and (4) a plunger.

The first tubular member can be characterized into three sections: an upper portion; a lower portion; and a spring housing portion disposed between the upper portion and lower body portion. The upper portion comprises a first release latch and a second release latch and a bearing seat disposed at least below the first and second release latch and aligned therewith. The first and second release latch are generally disposed on opposite sides of the upper portion and when closed, restrict vertical movement of the second tubular member upward with respect to the first tubular member. When the first and second release latches are pushed outwardly, they are in an open configuration thereby permitting vertical movement of the second tubular member upward with respect to the first tubular member. The bearing seat provides a surface to limit the vertical movement of the second tubular member downward with respect to the first tubular member. The upper portion may further comprise a pair of grip tabs protruding outwardly from the upper portion of the first tubular member. A user's fingers can be placed underneath the grip tabs to secure the syringe device during injection. The upper portion further comprises a first visual cue to indicate the position of the release latches. In certain embodiments, the grip tabs are aligned with the release latches and provide the first visual cue themselves or can present a marking thereon to provide the first visual cue. In other embodiments, the first visual cue is a marking otherwise presented on the upper portion positioned to indicate the location of the release latches.

The spring housing portion of the first tubular member comprises an annular groove sufficient to carry a spring. In certain embodiments, the spring housing portion is characterized by a first outer wall of the first tubular member and an inner wall spaced apart from the outer wall such that the space between the inner wall and outer wall provides the annular groove.

The body portion of the first tubular member provides the protective shield that covers the needle following engagement of the safety device. The internal cavity of the body portion is free of any encumbrances to prevent downward movement of the second tubular member after the safety device has been engaged such that the second tubular member may return to its original position for a subsequent injection.

The second tubular member is movable vertically within the inner annular cavity of the first tubular member from an injection position to a post-injection position. The second tubular member comprises a first upper flange and a second upper flange at its proximal end and a lower flange at its distal end. The first upper flange is aligned with each of the first and second release latches such that when the first and second release latches are in a closed configuration, the first upper flange is disposed beneath the first and second release latches in a manner to prevent the second tubular member from moving vertically upward beyond the first and second release latches. The second upper flange rests on the bearing seat of the upper portion of the first tubular member thereby preventing the second tubular member from moving vertically downward with respect to the first tubular member when the device is in the injection position. In certain embodiments, the second upper flange may also provide a ceiling for securing the spring in the spring housing portion while in the injection position and provides a surface by which the spring may apply force to the second tubular member directing its movement upward in the post-injection position. The lower flange is sufficient to contact the first tubular member at a distal end of the spring housing portion when the spring is engaged thereby preventing further vertical upward movement of the second tubular member with respect to the first tubular member. Alternatively, the first tubular member may comprise an additional flange located within the internal cavity of the body portion that engages the lower flange of the second tubular member and prevents further upward movement of the second tubular member. At any rate, the additional flange must be positioned to permit the needle to be contained within the body portion in a post-injection position.

The syringe is disposed in the inner annular cavity of the second tubular member and is in a fixed position with respect to the second tubular member. The syringe comprises an endpiece sufficient to receive and secure a needle thereto. The syringe may be fixed to the second tubular member by any appropriate means. In one embodiment, the syringe comprises a lip at its most proximal end extending outwardly and positioned between the first upper flange and second upper flange of the second tubular member.

In select embodiments, the needle is made of a plastic fiber or alternative flexible material (e.g., a monofilament) intended not to pinch or harm a subject employing the device. The simulated injection may be carried out on a subject or alternative injection material. The term "subject"

as used herein refers to a mammal, and in particular a human. The injection material can be any material suitable for injection material as recognized by one of skill in the art, including for instance an injection pad.

The plunger is movable vertically within the syringe and comprising a proximal end and a distal end carrying a piston to drive the fluid out of the syringe. The proximal end comprises a user contact surface and a release flange disposed distally from the user contact surface. The release flange extends outwardly from the plunger at a first distance on no more than two opposite sides of the plunger, wherein the first distance is sufficient to engage the release latches and push them outward thereby permitting vertical movement of the second tubular member upward once downward pressure is removed from the user contact surface. Thus, there are at least two other opposite sides of the plunger where there is either no release flange or wherein the release flange extends outwardly from the plunger at a second distance, wherein the second distance is not sufficient to engage the release latches. The user contact surface provides a point of contact for the user to apply pressure downward on the plunger to inject any fluid contained in the syringe. In addition, the user contact surface comprises a second visual cue; wherein the second visual cue indicates the portions of the release flange that extend outwardly at the first distance. In this way, the user can orient the plunger in the syringe to either prevent the release flange from engaging the release latches or can orient the release flange to engage the release latches by simply turning the plunger to align the second visual cue with the first visual cue (engagement) or to remove such from alignment (disengagement). Generally, this would only require the user to turn the plunger 90° to move between the engaged position and the disengaged position.

The present invention further includes a method of operating the reusable safety syringe device. The method comprising the steps of: (i) orienting the plunger such that the second visual cue is aligned with the first visual cue; (ii) simulating inserting the needle into a subject or a material; (iii) simulating injecting a fluid contained in the syringe into the subject or material by applying pressure on the user contact surface to push the plunger downward until the release flange engages the first and second release latches; (iv) simulating removing the needle from the subject or the material; (v) removing pressure from the user contact surface thereby causing the spring to expand to push the second tubular member upward thereby containing the needle in the body portion of the first tubular member; and (vi) rotating the plunger to a degree sufficient to prevent the release latch from engaging the first and second release latches. In specific embodiments, the method further comprises: (vii) orienting the plunger such that the second visual cue is aligned with the first visual cue; (viii) applying pressure on the user contact surface to push the second tubular member downward until the second upper flange comes to rest on the bearing seat and the first upper flange is disposed under the first and second release latches thereby securing the second tubular member to prevent upward vertical movement of the second tubular member relative to the first tubular member and causing the spring to return to the spring housing portion; and (ix) resetting the training device by pulling the plunger upward to an injection ready position. In specific embodiments, the method comprises repeating steps (i)-(ix) at least once.

DETAILED DESCRIPTION OF THE FIGURES

FIG. 5 depicts operation of an embodiment of the reusable safety syringe device of the present invention comprising the following steps: (A) depicts the device in a configuration ready for injection; (B) depicts the device at the end of the injection before downward pressure on the plunger has been removed; (C) depicts the device following injection when downward pressure on the plunger has been removed and the safety device has been engaged; (D) depicts rotating the plunger following injection to prepare the device for subsequent use; (E) depicts the device configuration for locking the second tubular member in place with respect to the first tubular member; (F) depicts the plunger moving upward to return to its initial axial position; and (G) depicts rotating the plunger so that it is in the proper alignment to engage the release latches upon depressing the plunger thereby returning the device to an injection-ready configuration as shown in (A).

DETAILED DESCRIPTION OF THE INVENTION

Figure 1A:
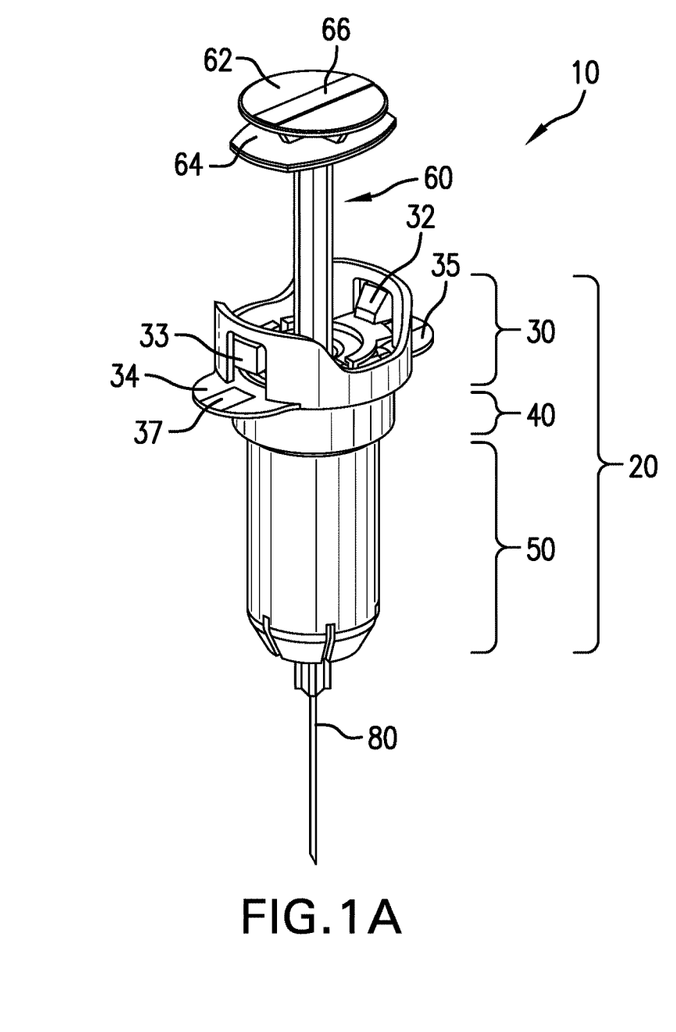
FIG. 1A depicts one embodiment of the reusable safety syringe device of the present invention.
Figure 1B:
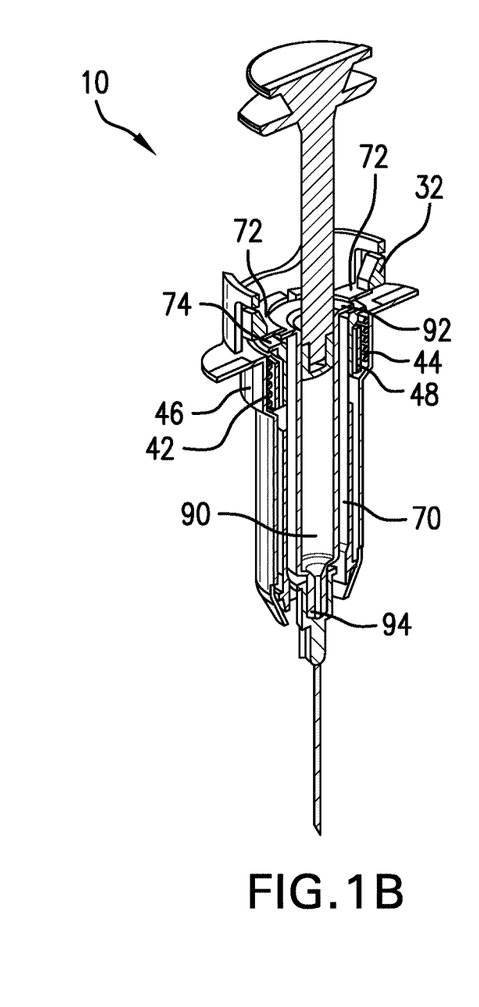
FIG. 1B is a cross section of the reusable safety syringe device depicted in FIG. 1A.
Figure 2A:
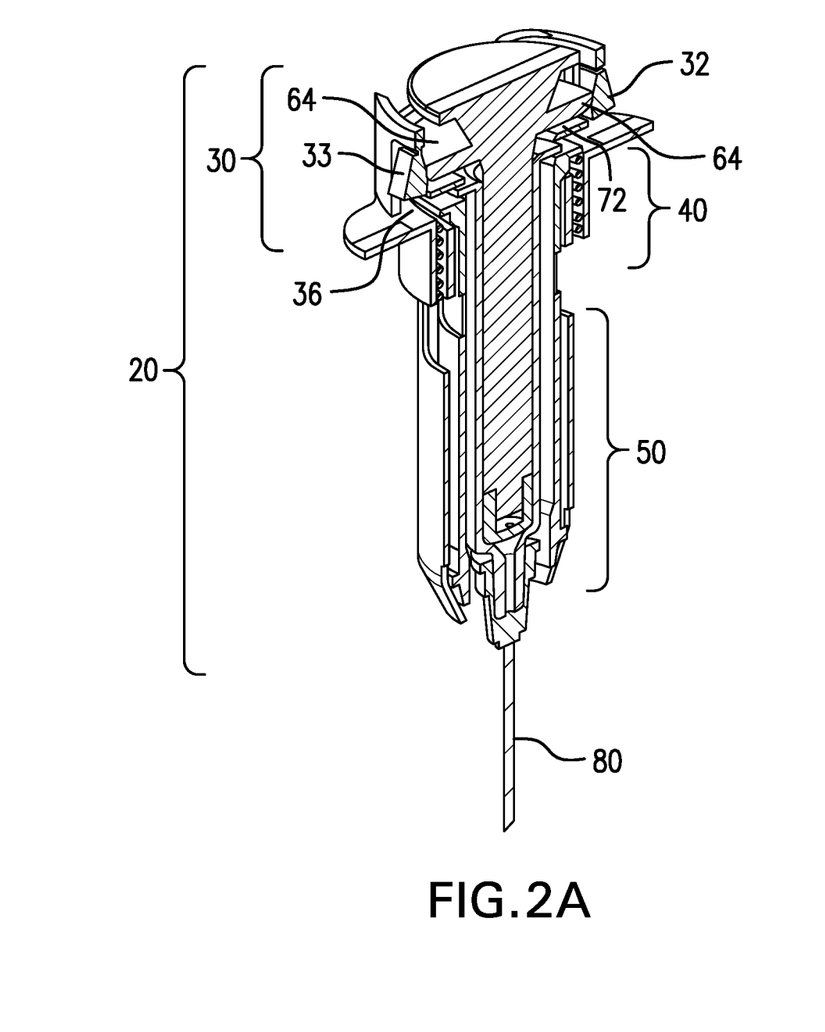
FIG. 2A is a cross section of an embodiment of the reusable safety syringe device during the injection.

One embodiment of the reusable safety syringe device of the present invention is depicted in FIGS. 1A, 1B, 2A, and 2B. The device 10 comprises a standard syringe 90 for injecting a liquid. Syringe 90 has an open proximal end provided with a lip 92 and a distal end providing an end piece 94 sufficient to secure needle 80, an optional syringe closure plug (not shown) or an optional needle carrier (not shown). The syringe 90 includes a plunger 60 moveable vertically therein between a pre-injection position as shown in FIGS. 1A and 1B and a post-injection position as shown in FIG. 2A. Plunger 60 has a proximal end comprising user contact surface 62 and release flange 64, and a distal end inside the cavity.

The device 10 further comprises safety components referred to herein as first tubular member 20 and second tubular member 70 housed inside first tubular member 20 and substantially coaxial therewith. The first tubular member 20 and the second tubular member 70 are movable axially relative to each other between a first position, referred to as a locked position of the needle, as shown in FIGS. 1A, 1B and 2A, and a second position, referred to as an engaged position of the needle, as shown in FIG. 2B.

First tubular member 20 comprises upper portion 30, spring housing portion 40, and body portion 50. It should be understood that these portions are defined herein for purposes of orientation of various aspects of the device and is not intended to require the device to possess distinct and visually separable portions. Upper portion 30 comprises release latches 32, 33 positioned diametrically opposite. Release latches 32, 33 are elastically deformable in a radial direction. Release latches 32, 33 are depicted in FIGS. 1A and 1B in a locked configuration such that they protrude inwardly and prevent upward movement of second tubular member 70 at first upper flange 72 and in an open configuration as shown in FIG. 2A where release flange 64 engages release latches 32, 33 causing them to protrude outwardly. Upper portion 30 may further comprise grip tabs 34, 35 designed to be gripped by the fingers of a user to simulate the injection of a liquid by axially moving plunger 60 towards grip tabs 34, 35.

Spring housing portion 40 may be constructed in a number of different manners. In one embodiment, spring housing portion 40 is formed by outer wall 46 and inner wall 48 where spring 42 is housed in groove 44 between outer wall 46 and inner wall 48. Groove 44 serves to position spring 42 both axially and radially. Spring 42 bears against second upper flange 74 formed on second tubular member 70, and on an inner seat (not shown) projecting inwardly from first tubular member 20 and positioned at the bottom of groove 44 housing spring 42. In other embodiments, inner wall 48 may not be necessary so long as the second tubular member 70 is sufficient to contain spring 42 between it and outer wall 46.

Figure 2B:
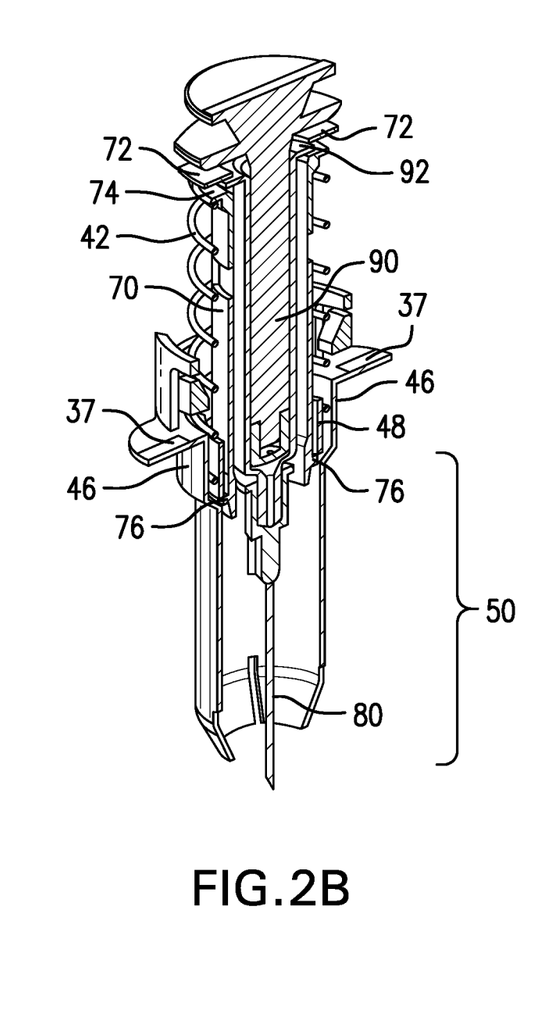
FIG. 2B is a cross section of an embodiment of the reusable safety syringe device following injection with the safety shield engaged.

Body portion 50 provides the protective sheath when device 10 is in the engaged position as shown in FIG. 2B thereby encompassing needle 80.

Syringe 90 is housed in second tubular member 70. More particularly, syringe 90 is prevented from moving axially in second tubular member 70 by lip 92 positioned between first upper flange 72 and second upper flange 74 of second tubular member 70. Where appropriate, the radial and transverse clearances between lip 92 and the housing formed by first and second upper flanges 72 and 74 can be limited by cooperation between complementary shapes.

Second upper flange 74 also serves to prevent downward axial movement of second tubular member 70 with respect to first tubular member 20 by engaging bearing seat 36 on upper portion 30 as shown in FIGS. 2A and 2B.

Second tubular member 70 further comprises a diametrically-opposite pair of lower flanges 76 serving to co-operate with inner wall 48 of spring housing portion 40 for preventing further upward axial movement of second tubular member 70 with respect to first tubular member 20 as shown in FIG. 2B. In the absence of inner wall 48, a pair of abutments (not shown) can extend from outer wall 46 to perform the same function.

Figure 3A:
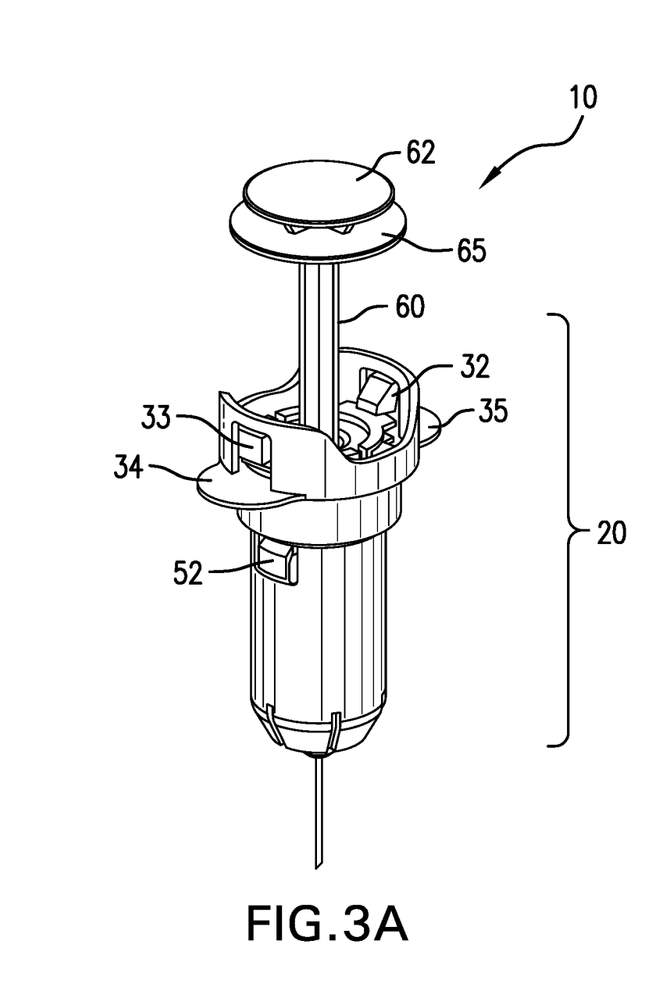
FIG. 3A depicts an embodiment of a safety syringe device configured for a single use.
Figure 3B:
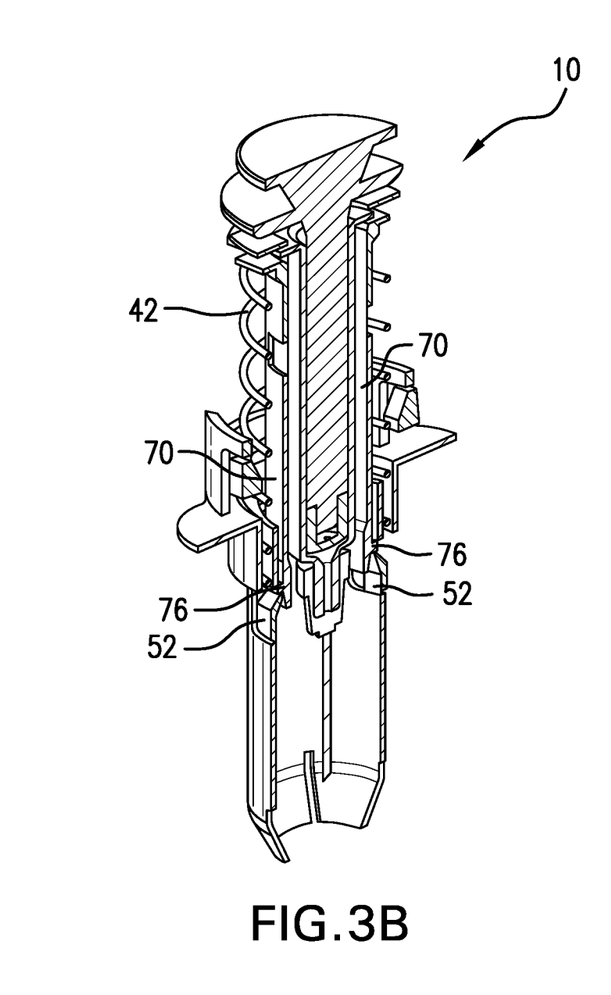
FIG. 3B is a cross section of an embodiment of a safety syringe device configured for a single use following injection.
Figure 4A:
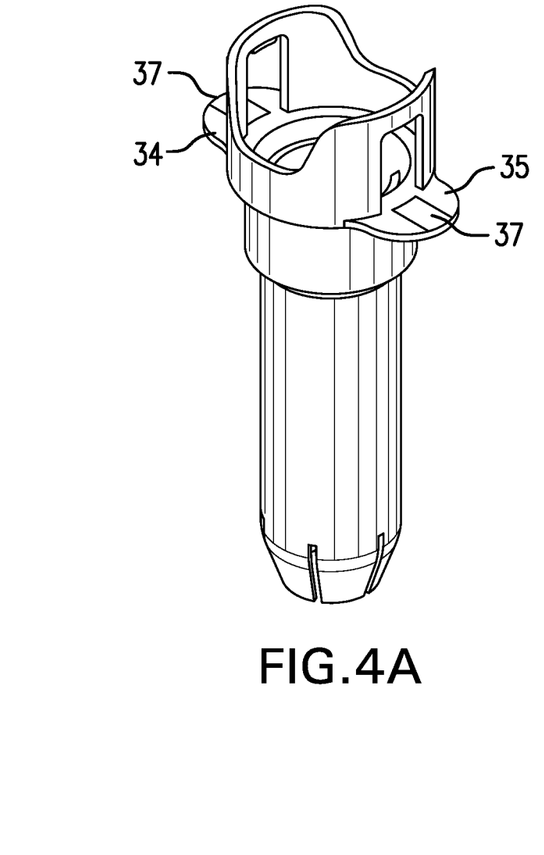
FIG. 4A depicts the first tubular member of an embodiment of the reusable safety syringe device of the present invention to highlight the modifications made to the single use device.
Figure 4B:
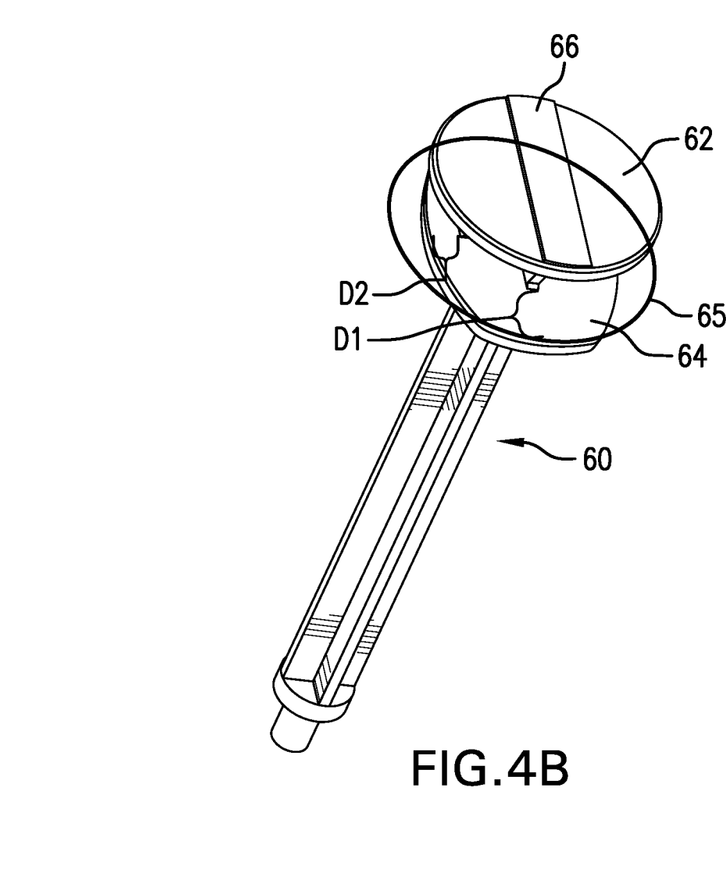
FIG. 4B depicts the plunger of an embodiment of the reusable safety syringe device of the present invention to highlight the modifications made to the single use device.
Figure 5A:
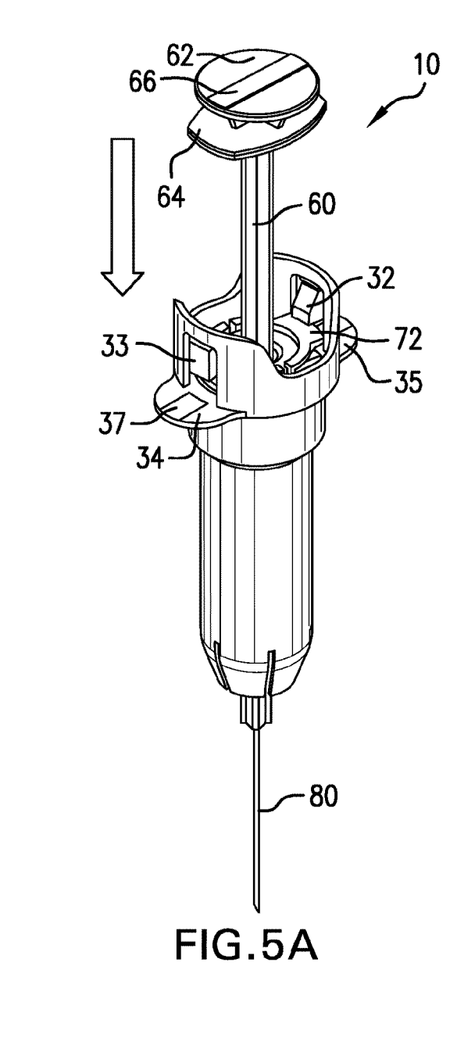
Figure 5B:
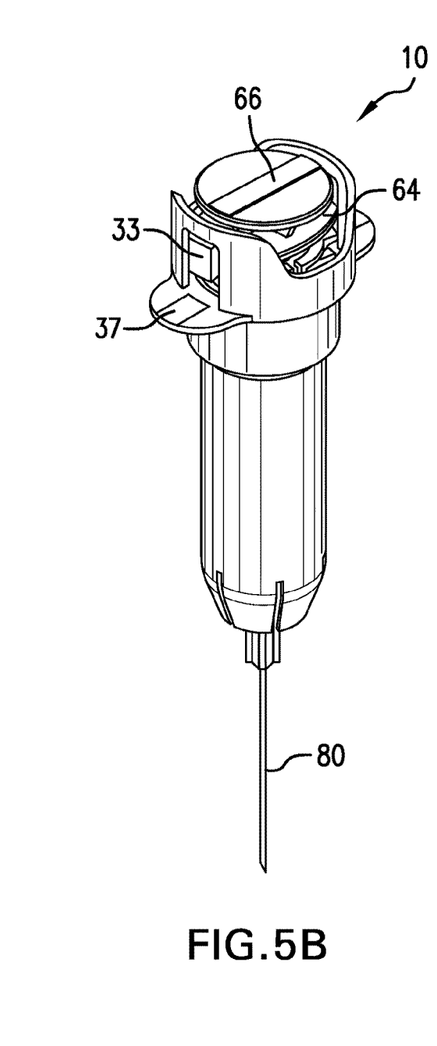
Figure 5C:
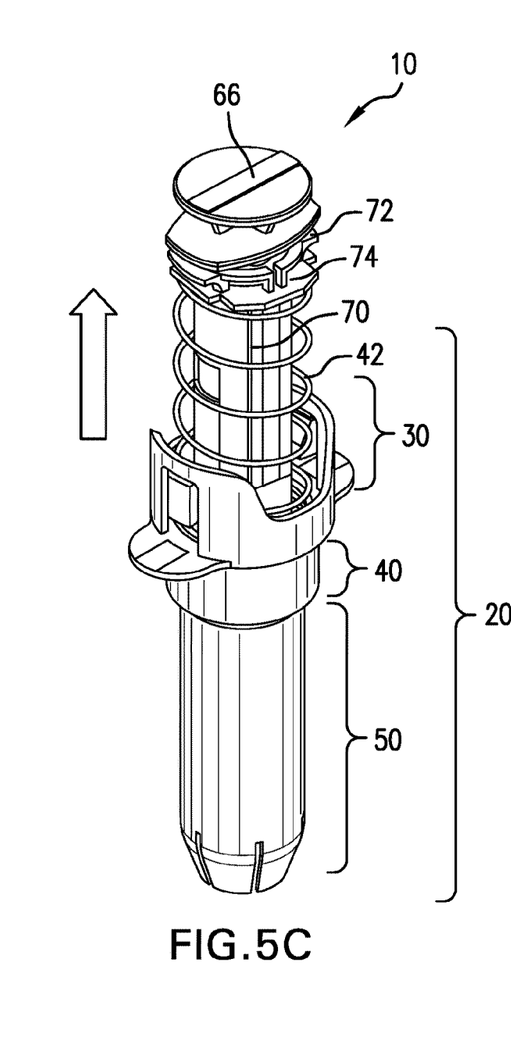
Figure 5D:
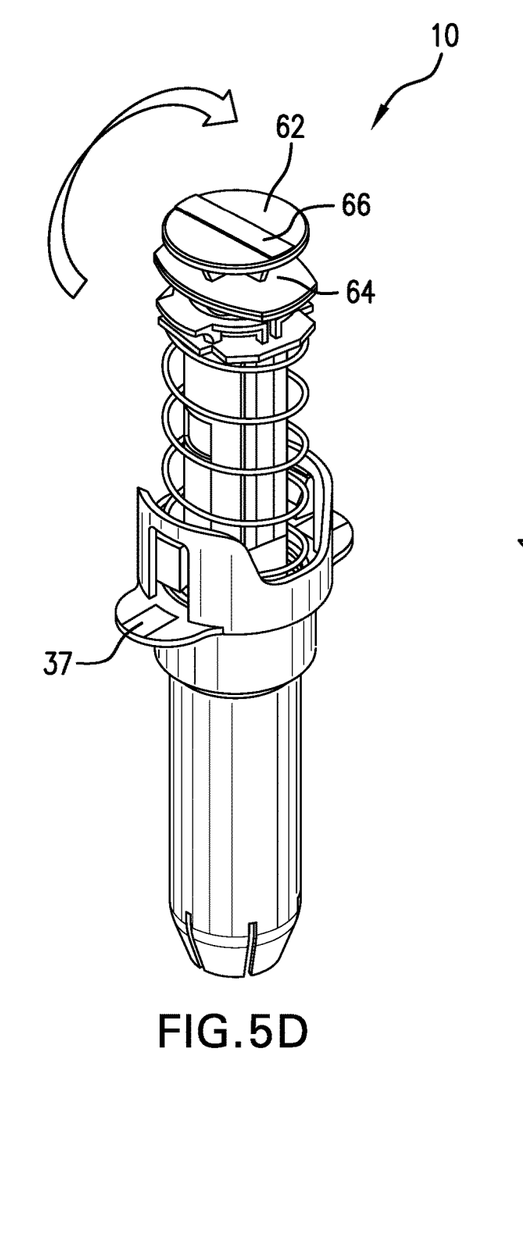
Figure 5E:
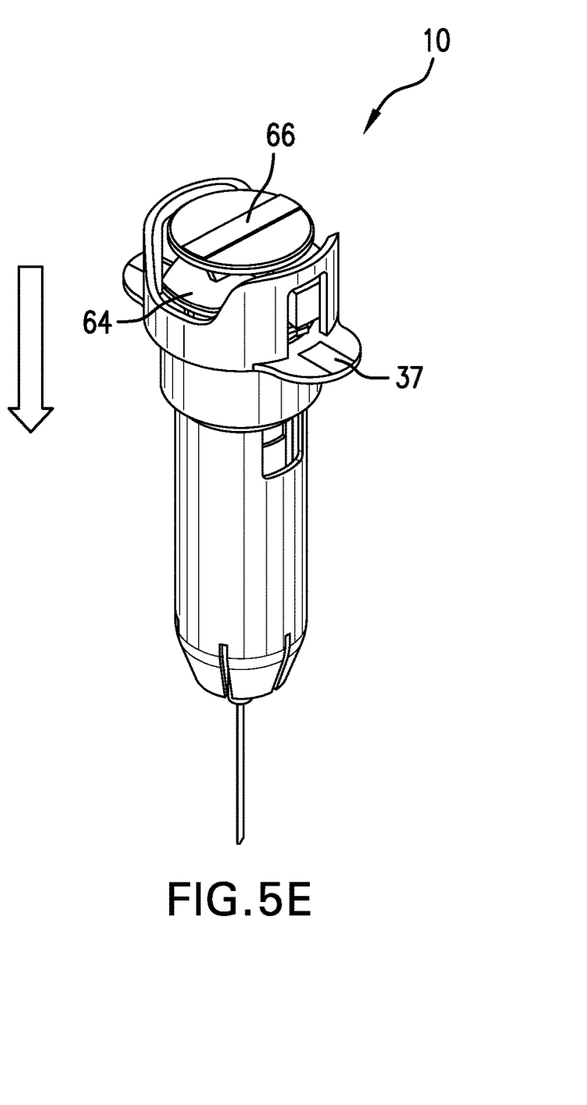
Figure 5F:
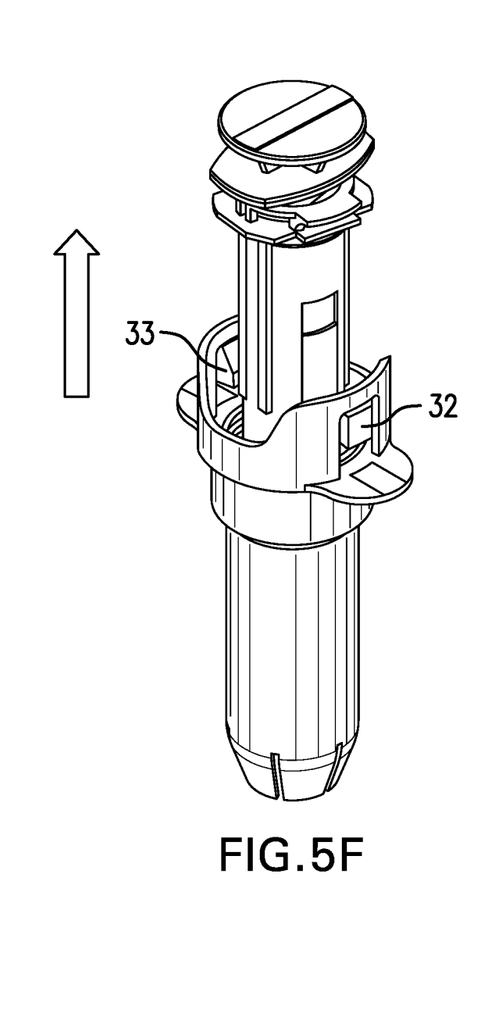
Figure 5G:
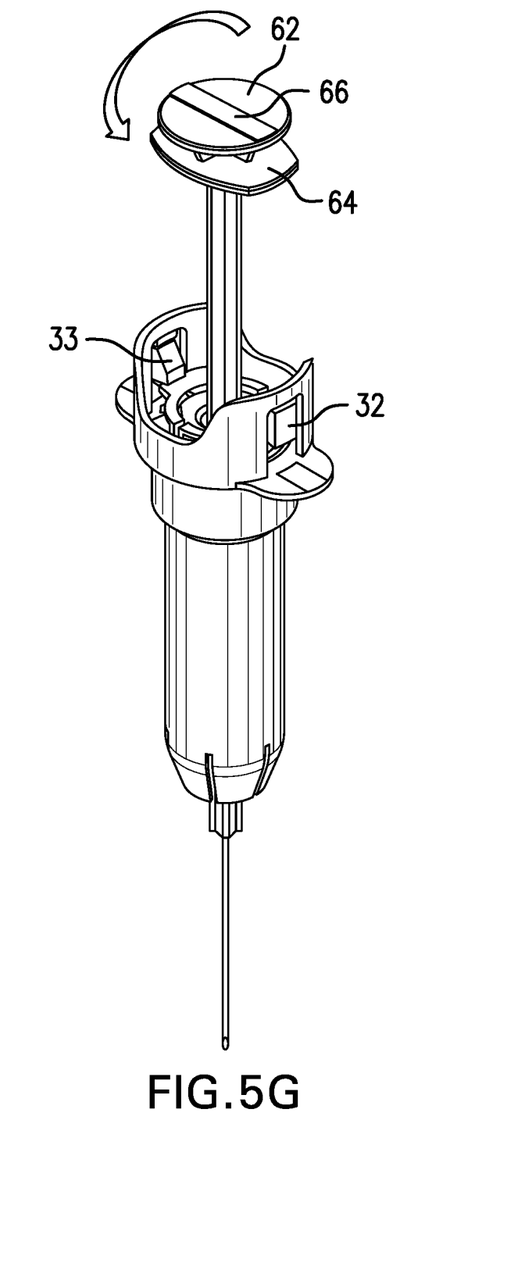

Referring now to FIGS. 3A and 3B, an example of a safety syringe device configured for only a single use is provided. In particular, release flange 65 extends radially an equal distance from plunger 60 on all sides such that there is no orientation of plunger 60 where release flange 65 will avoid engaging release latches 32, 33. This prevents the ability to re-lock the axial position of second tubular member 70 in the locked position for subsequent simulated injections, instruction and learning. Accordingly, one modification provided in the present invention is to modify release flange 65 by either removing material on one pair of opposite sides of plunger or by reducing the amount of material on one pair of opposite sides such as shown in FIG. 4B. Doing so results in a pair of opposite sides of release flange 64 extending radially at a first distance D1 where such distance is sufficient for these portion of release flange 64 to engage release latches 32, 33 as shown in FIG. 2A. In this instance, the other pair of opposite sides of release flange 64 are at a second distance D2 which is not sufficient to engage release latches 32, 33.

The single use device also has locking means 52 for locking the first tubular member 20 in the retracted or engaged position as shown in FIG. 3B. Once second tubular member 70 is forced upward axially by spring 42 past locking means 52, it is prevented from further upward axial movement by either inner wall, or in the absence thereof, by a pair of abutments as described above, and prevented from further downward axial movement by locking means 52. The reusable safety device 10 of the present invention does not include locking means 52 as shown in FIG. 4A so that second tubular member 70 may be moved axially downward to the original locked position for subsequent simulated injections, instruction and learning.

The reusable safety syringe device of the present invention further comprises a pair of visual cues to assist the user in determining the proper orientation of release flange 64 with respect to release latches 32, 33 for the intended use. As shown herein, a visual cue 66 is disposed on user contact surface 62 and visual cue 37 is located on grip tabs 34, 35. When visual cue 66 is aligned with visual cue 37, device 10 is ready to simulate an injection and provide instruction of proper use of the actual passive safety syringe. When visual cues are not aligned, second tubular member 70 can be relocked in the injection position as release latches 32, 33 will not be engaged by release flange 64. Although the visual cue is depicted herein as a solid line, it should be understood that release flange 64 can act as the visual cue and grip tabs 34, 35 can act as the visual cue 37 so long as grip tabs are aligned with release latches 32, 33. Moreover, visual cues may be presented in any form such as notches, holes, dots, or the like so long as they signify to the user when the release flange 64 will or won't engage the release latches 32, 33.

The principal stages in the operation of reusable device 10 is outlined below with reference to FIG. 5. In step A of FIG. 5, device 10 is in a locked configuration and ready for simulated injection. As depicted, visual cue 66 is aligned with visual cue 37 which indicates that release flange 64 is in the proper orientation to engage release latches 32, 33. User will then grasp the device with fingers under grip tabs 34, 35 and thumb on user contact surface 62 and apply downward pressure on plunger 60 until the would be fluid is deployed through the needle 80 and into the subject or appropriate training material (not shown) resulting in the fully injected position depicted in step B. In this position, release flange 64 engages release latches 32, 33 such that once the user removes pressure from plunger 60, second tubular member (not shown) is able to be forced upward by spring 42 until lower flange (not shown) engages inner wall (not shown) to stop upward movement of second tubular member (not shown) relative to first tubular member 20 as shown in step C of FIG. 5. In this position, needle 80 is completely contained in the inner annual cavity of body portion 50 of first tubular member 20. Without the modifications described herein, the user would then discard device 10 following this use considering second tubular member cannot be re-locked into the position shown in step A of FIG. 5.

Steps D-G now describe the reusable operation of device 10. Referring now to step D, the user turns plunger a quarter turn (90°) in either direction so that the visual cues are no longer aligned. Considering that the locking means are no longer present, user can apply downward pressure to user contact surface 62 and move second tubular member 70 (and syringe) axially downward until second upper flange contacts bearing seat and first upper flange is secured under release latches 32, 33 returning device 10 to its locked position as shown in step E. The user pulls plunger 60 upward to prepare the trainer for another practice simulation as shown in step F. User will then turn plunger 60 another quarter turn to align the visual cues or otherwise to align release flange 64 in a position to engage release latches 32, 33 as shown in step G. The device is now in the ready position for a subsequent simulated injection. This process can be repeated as many times as desired which provides a highly effective training tool.

The invention is not limited to the embodiment described above. One of ordinary skill in the art could appreciate modifications to the embodiment described above that will perform the same reusable function.

What is claimed is:

1. A safety syringe injector device for use in patient training comprising:
    a first tubular member having an inner annular cavity comprising an upper portion, a spring housing portion, and a body portion, wherein the body portion is positioned distally with respect to the spring housing portion and the upper portion is positioned proximately with respect to the spring housing portion, wherein the upper portion comprises a first release latch, a second release latch, and a bearing seat, the first tubular member further comprising a first visual cue, wherein the first visual cue indicates a position of one or both of the first and second release latches, wherein the first and second release latches are diametrically opposed, wherein the bearing seat is disposed below the first and second release latches, and wherein the spring housing portion provides an annular groove housing a spring;
    a second tubular member having an inner annular cavity movable vertically within the inner annular cavity of the first tubular member from a first position to a second position, wherein in the first position, a distal end of the second tubular member is positioned at a distal end of the body portion of the first tubular member such that the second tubular member is contained substantially within the inner annular cavity of the first tubular member, and wherein in the second position, the distal end of the second tubular member is positioned at the spring housing portion such that only a distal portion of the second tubular member is contained within the inner annular cavity of the first tubular member, and wherein the body portion does not carry any encumbrances to prevent the second tubular member from moving vertically from the first position to the second position or from the second position to the first position;
    a syringe comprising a reservoir capable of holding a liquid, the syringe disposed within the inner annular cavity of the second tubular member and fixed vertically with respect to the second tubular member, the syringe further comprising an end piece configured to receive and secure a needle; and
    a plunger movable vertically within the syringe and comprising a proximal end and a distal end, wherein the proximal end comprises a user contact surface and a release flange disposed distally from the user contact surface, wherein the release flange extends outwardly from the plunger at a first distance, extending past the user contact surface, on no more than two opposite sides of the plunger and wherein the remaining sides of the release flange extend outwardly from the plunger at a second distance, not extending past the user contact surface, wherein the first distance is sufficient to engage the first and second release latches and push them outward, and wherein the second distance is not sufficient to engage the first and second release latches, the plunger comprising a second visual cue, wherein the second visual cue is positioned to indicate the release flange or a portion of the release flange extending outwardly from the plunger at the first distance, wherein the release flange or the portion of the release flange is positioned to engage the first and second release latches when the second visual cue is in an aligned position with the first visual cue, and wherein the release flange or the portion of the release flange is not positioned to engage the first and second release latches when the plunger is rotated 90 degrees from the aligned position.

2. The safety syringe injector device of claim 1 wherein the first visual cue is on the upper portion of the first tubular member.

3. The safety syringe injector device of claim 1 wherein the second tubular member comprises a first upper flange and a second upper flange at a proximal end of the second tubular member, and a lower flange at the distal end of the second tubular member, wherein the first upper flange is aligned with each of the first and second release latches such that when the first and second release latches are in a closed configuration and the second tubular member is in the first position, the second tubular member is prevented from moving vertically beyond the first and second release latches due to the first upper flange, and wherein the second upper flange rests on the bearing seat of the upper portion of the first tubular member when the second tubular member is in the first position, wherein the second upper flange further prevents the spring from expanding beyond the spring housing portion when the first upper flange is disposed below the first and second release latches, and wherein the lower flange is sufficient to contact the first tubular member at a distal end of the spring housing portion when the spring is engaged and the second tubular member is in the second position thereby preventing further vertical upward movement of the second tubular member with respect to the first tubular member.

4. The safety syringe injector device of claim 3 wherein the syringe further comprises a lip at a proximal end of the syringe, wherein the lip is disposed between the first upper flange and the second upper flange of the second tubular member.

5. The safety syringe injector device of claim 1 wherein the first and second release latches are the first visual cue.

6. The safety syringe injector device of claim 1 wherein the second visual cue is the release flange or a portion thereof having the first distance.

7. The safety syringe injector device of claim 1 wherein the second visual cue is a marking on the user contact surface.

8. The safety syringe injector device of claim 1 wherein the first tubular member further comprises two grip tabs extending outwardly from the first tubular member.

9. The safety syringe injector device of claim 8 wherein the first visual cue is a marking on the two grip tabs.

10. The safety syringe injector device of claim 8 wherein the two grip tabs are positioned distally from the first and second release latches and aligned therewith.

11. The safety syringe injector device of claim 10 wherein the first visual cue is the two grip tabs.

12. A method for operating the safety syringe injector device of claim 3 comprising the following steps:

(i) orienting the plunger such that the second visual cue is aligned with the first visual cue;
(ii) simulating inserting the needle into a subject or a material;
(iii) simulating injecting a fluid contained in the syringe into the subject or the material by applying pressure on the user contact surface to push the plunger downward until the release flange engages the first and second release latches;
(iv) simulating removing the needle from the subject or the material;
(v) removing pressure from the user contact surface thereby causing the spring to expand to push the second tubular member upward thereby containing the needle in the body portion of the first tubular member; and
(vi) rotating the plunger to a degree sufficient to prevent the release flange from engaging the first and second release latches.

13. The method of claim 12 further comprising the following steps:
(vii) orienting the plunger such that the second visual cue is aligned with the first visual cue;
(viii) applying pressure on the user contact surface to push the second tubular member downward until the second upper flange comes to rest on the bearing seat and the first upper flange is disposed under the first and second release latches thereby securing the second tubular member to prevent upward vertical movement of the second tubular member relative to the first tubular member and causing the spring to return to the spring housing portion;
(ix) resetting the safety syringe injector device by pulling the plunger upward to an injection ready position.

14. The method of claim 13 where steps (i)-(ix) are repeated at least once.

* * * * *

UNITED STATES PATENT AND TRADEMARK OFFICE
CERTIFICATE OF CORRECTION

PATENT NO. : 11,587,463 B2
APPLICATION NO. : 16/338797
DATED : February 21, 2023
INVENTOR(S) : Basile et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 994 days.

Signed and Sealed this
Fourteenth Day of January, 2025

Derrick Brent
*Acting Director of the United States Patent and Trademark Office*